United States Patent [19]

Hammond et al.

[11] Patent Number: 4,945,176

[45] Date of Patent: Jul. 31, 1990

[54] FLUORINATED LASER DYES

[75] Inventors: Peter R. Hammond, Livermore, Calif.; James F. Feeman, Wyomissing, Pa.

[73] Assignee: The United States of America as represented by the United States Department of Energy, Washington, D.C.

[21] Appl. No.: 373,316

[22] Filed: Jun. 8, 1989

[51] Int. Cl.$^5$ ............................................. C07D 311/82
[52] U.S. Cl. ..................................... 549/227; 549/226
[58] Field of Search ........................ 549/390, 226, 227

[56] References Cited

FOREIGN PATENT DOCUMENTS 3531272 3/1987 Fed. Rep. of Germany .
0952925 8/1982 U.S.S.R. .

Primary Examiner—Richard L. Raymond
Assistant Examiner—Amelia A. Owens
Attorney, Agent, or Firm—Miguel Valdes; Roger S. Gaither; William R. Moser

[57] ABSTRACT

A novel class of dye is disclosed which is particularly efficient and stable for dye layer applications, lasing between 540 and 570 nm.

8 Claims, No Drawings

FLUORINATED LASER DYES

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to a novel class of dyes which will lase efficiently and stably at a peak wavelength between 540 and 570 nm.

In U.S. Pat. No. 4,622,400 there is disclosed a method of preparing m-aminophenols which are useful for preparation of dyes, particularly for the preparation of rhodamine class dyes.

SUMMARY OF THE INVENTION

It is an object of the present invention to provide a novel class of dyes which is useful in dye laser applications and which lase at wavelengths between 540 and 570 nm.

It is another object of the present invention to provide a novel class of dyes which lase between 540 and 570 nm which can be prepared from relatively inexpensive materials and which exhibit lasing efficiency and photochemical stability for extended operation.

These and other objects and advantages of the invention will be apparent in the description of the specific embodiments thereof, given by way of example, to enable one skilled in the art to readily practice the invention which is described hereinafter.

In general, the present invention is directed to a novel class of dyes of the formula I:

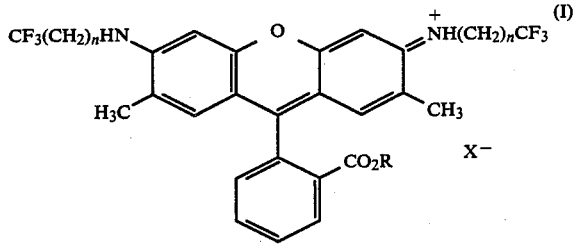

wherein R is hydrogen or a linear or branched alkyl group of 1 to 10 carbon atoms, n is an integer from 1 to 4 and X is an anion. Preferably R is a linear or branched alkyl group of 1 to 4 carbon atoms, and n is 1 or 2.

DETAILED DESCRIPTION OF THE INVENTION

Compounds according to the present invention may be made by any of several routes. The preferred route begins with 3-amino-4-methylphenol (II).

The starting material, 3-amino-4-methylphenol (II), is treated with an appropriate alkylating agent, preferably, 3,3,3-trifluoro-1-chloropropane or trifluorethyl p-toluenesulfonate, to make the alkylated intermediate (IIIA or IIIB). This intermediate (IIIA, B) can be condensed with excess phthalic anhydride and esterified to make the dyes according to the present invention.

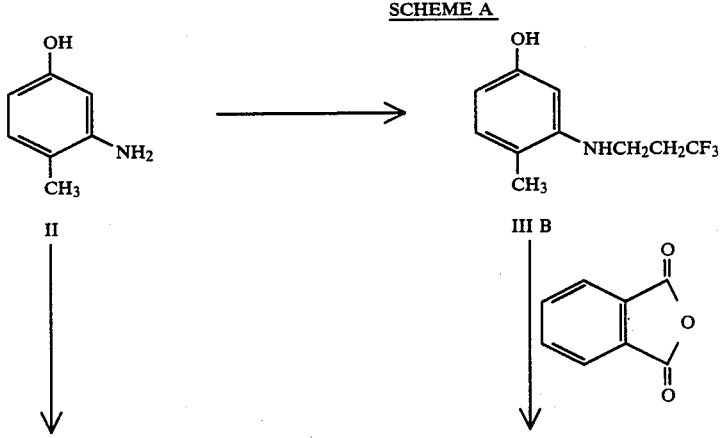

SCHEME A

SCHEME A

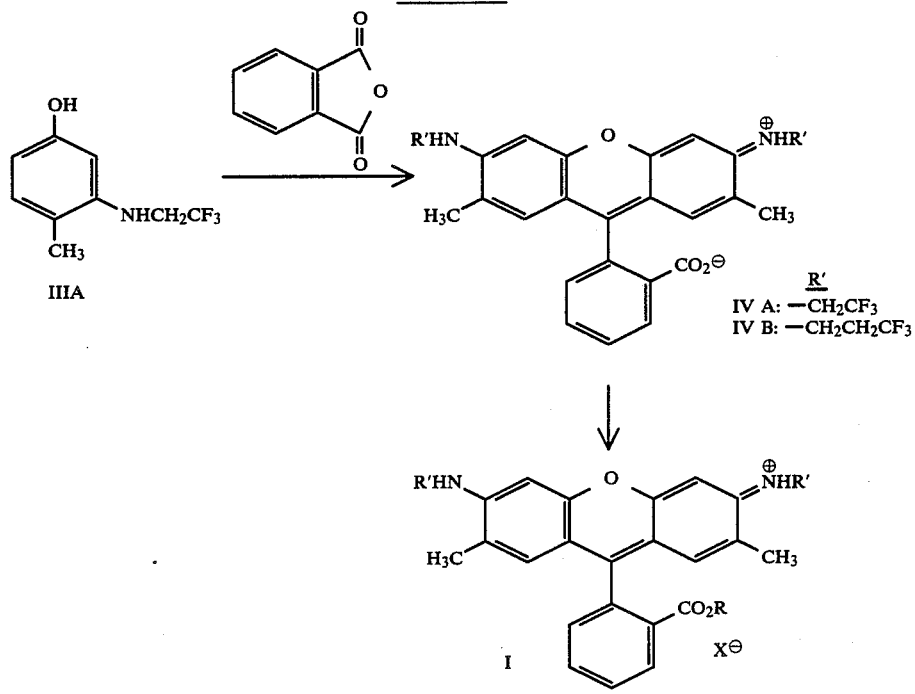

R'
IV A: —CH$_2$CF$_3$
IV B: —CH$_2$CH$_2$CF$_3$

The treatment of the phenol (III A, B) with excess of phthalic anhydride, followed by the addition of at least one other equivalent of IIIA or IIIB and condensation with 85% phosphoric acid, results in the dye (IV A, B). The zwitterions IV can then be esterified by conventional means, such as by treatment with alcohol and acid. The dyes can be converted to any desired salt by precipitation or crystallization with a desired counter-ion, such as, by precipitation with fluoroboric acid to produce the fluoroborate salt. The anion X is preferably inorganic, such as halide, sulfate, perchlorate, fluoroborate, borate, phosphate and the like. Chloride, perchlorate and fluoroborate are salts preferred because of their ease of preparation, ease of use and convenience.

In general, conditions for condensing phenols with phthalic anhydride are disclosed in Patent No. 4,622,400, the disclosure of which is incorporated herein by reference in its entirety.

The dyes according to the present invention are particularly useful in dye lasers. They can be pumped by pulsed excitation sources (doubled neodymium laser, copper vapor laser, flashlamp) or by a continuous wave argon ion laser. Typically, the dyes are mixed in ethanol at a dye concentration of 0.5–2.5 grams of dye per liter of solvent. A preferred dye of the formula I, (n=2, as the fluoroborate salt) according to the present invention, wherein R is methyl (molecular weight 652.4), exhibits $\Gamma_{max}$ at 522 nm (its absorption maximum) of $1.128 \times 10^5$ The solubility is 2.3 grams per liter of 95% ethanol at 5.C, while at 78.5° C. it is 20.0 grams per liter. These ethanol solutions lase efficiently and stably in a copper vapor laser pumped oscillator at peak wavelengths of 544 and 563 nm for n=1 and 2, respectively. An ethylene glycol solution of another preferred dye (n=1) lases with peak wavelength 560 nm in an argon pumped continuous wave dye laser. The performance is as efficient as for the known dye 9-(2-carboxyphenyl)-3,6-bisamino-xanthylium chloride, yet is over twenty times more stable.

It will be appreciated that the solvents which may be utilized, the concentration of the dye in a particular solvent and the nature and type of pumping laser utilized will depend upon the intended application of the dye laser and upon the lasing apparatus in which the dye is to be utilized. The foregoing information is thus provided as a matter of guidance to those of ordinary skill in the art who can thus readily adjust the appropriate concentration and solvent to the intended dye laser.

The following examples are presented to help in the better understanding of the subject matter and for purpose of illustration. They are not intended to be construed as limiting to the precise form of the invention disclosed or to limit the scope of the invention in any manner or means.

EXAMPLE 1

PREPARATION OF 3-TRIFLUOROETHYLAMINE-4-METHYL-PHENOL(OH1)

3-Amino-4-methylphenol (9.84 g; 0.08 mole) and trifluoroethyl tosylate (20.32 g; 0.08 mole) were mixed in a 500 ml round-bottomed flask and the flask purged with nitrogen. A short air condenser was added, the nitrogen stream was slowed and located towards the top of the condenser, and the flask was immersed in an oil bath at 200° C. A temperature in the range of 150°–250° C. is acceptable. After the molten reagents had been swirled to complete mixing, the heating was continued for five hours. The flask was allowed to cool and before the mixture had solidified, it was dispersed and dissolved in 200 ml of chloroform. Over four days a light brown precipitate of the tosylate salt of 3-amino-4-methylphenol appeared which was filtered off and recovered. The chloroform was extracted with 10% aqueous sodium hydroxide and the dark brown aqueous phase was extracted with chloroform 50 ml. Ice and concentrated hydrochloric acid (21 ml) were added to the aqueous phase and the brown oil was extracted into chloroform 100 ml plus 50 ml. The chloroform solution was washed with 1N hydrochloric and the chloroform layer was separated, dried with sodium sulfate, filtered and evaporated to give a brown gum that crystallized over a day 8.0 g (49%). Recrystallization from petroleum ether 60/80 gave white, fluffy needles mp. 64°–65° NMR (deuterodimethylsulfoxide): $\delta$ 8.86 (s, 1H, OH); 6.8–5.9 (m, 3H, ring protons) resolved as AB quartet at 6.74 (C-5 CH) and 6.01 (C-6 CH), J=8.0 Hz together with 6.13 (d, 1H, J=1.0 Hz, C-2 CH) which in turn coupled with the high-field half of the AB quartet; 5.33 (t, 1H, J=6.8 Hz, N-H); 4.0–3.7 (m, 2H, $CH_2$) resolved as two quadruplets, $J_{CF_3}$, $CH_2$ =9.6 Hz, $J_{CH_2}$, NH=6.8 Hz; 1.99 (s, 3H, $CH_3$). Anal. calc. for $C_9H_{10}F_3NO$: C, 52.68; H, 4.91; N, 6.83. Found: C, 52.58; H, 4.99; N, 6.80.

EXAMPLE 2
PREPARATION OF 9-(2-CARBOXYPHENYL)-3,6-BIS (TRIFLUOROETHYLAMINO)2,7-DIMETHYL-XANTHYLIUM HYDROXIDE, INNER SALT

3-Trifluoroethylamino-4-methylphenol (13.9 g; 0.068 mole) and phthalic anhydride (15.05 g; 0.102 mole - 1.5 mole equivalents) were heated in a 500 ml round-bottomed, single-neck flask equipped with a short, water-cooled reflux condenser in a 160° oil bath for three hours. A temperature in the range of 150°–180° C. is acceptable. At the start of the reaction the melt was swirled from time to time to facilitate mixing. A further batch of 3-trifluoroethylamino-4-methylphenol (14.0 g; 0.068 mole) was warmed with 85% phosphoric acid (25 ml plus 10 ml) and was transferred to the cooled reaction mixture. The flask was heated for four hours at an oil bath temperature of 170 ; again with occasional swirling. Methanol (170 ml; 25 ml per 0.01 M) was added to the cooled but still warm reactants and the mixture was refluxed for twenty minutes. Crystals appeared almost immediately and the liquid was stored in a 4° refrigerator overnight. Filtration, washing with cold methanol, and drying gave 25.1 g of red-orange crystals. A second crop 0.9 g (total yield 73%) came from the filtrate kept several days at 4° C.

EXAMPLE 3
PREPARATION OF 9-(2-METHOXYCARBONYLPHENYL)-3,6-BIS (TRIFLUOROETHYLAMINO)-2,7-DIMETHYL-XANTHYLIUM FLUOROBORATE

To 26 g of the zwitterion (from Example 2) in a one liter, three-necked round-bottomed flask equipped with stirrer and efficient water condenser having a glass-wool plug were added methanol 500 ml containing sulfuric acid 25 ml. The mixture was stirred and refluxed for more than 54 hours (in this case 94 hours) and esterification was 97% complete. Reaction was monitored by thin layer chromatography on alumina, eluting with isopropanol-zwitterion $R_f$ 0.35, methyl ester $R_f$ 0.65. The mixture was filtered hot through Whatman No. 4 filter paper and 60% aqueous flouroboric acid (9.3 ml; 50% excess) was added. Crystals of the fluoroborate deposited from the cooled solution, which was stored for two days at 4°. Filtration, washing with cold methanol/water (1:1, v:v) and air drying gave 19.5 g of orange crystals. Two further crops were obtained by storing the filtrate for a week at −8°. Combined samples were dried in a vacuum oven at 60° for three hours (23.3 g, 75%). The material recrystallized from methanol/water (1:1, v:v, 150 ml/g) as orange crystals with a green sheen, mp. 312°–313° with previous softening at 304°. NMR (deuterodimethylsulfoxide): $\delta$ 8.4–7.47 (m, 6H) resolved as 8.03 (broad t, 2H, J=6.8 Hz, N—H) and the rest as ring protons of the pendant aromatic group; 7.42 and 6.97 (d, 4H, xanthylium ring protons 1, 4, 5, 8): 4.48 (broad q, 4H, J=7.8 Hz, $CH_2$); 3.5B(s, 3H, O—$CH_3$); 2.17 (s, 6H, $CH_3$). Anal. calc. for $C_{27}H_{23}N_2OBF_{10}$: C, 51.94; H, 3.71; N, 4.49. Found: C,51.92; H, 3.79; N, 4.40. Absorption in 190 proof alcohol: $\epsilon_{max}$ at 509 nm $1.036 \times 10^5$; $\epsilon_{488}$ $0.401 \times 10^5$; $\epsilon_{510.6}$ $1.033 \times 10^5$; $\epsilon_{514}$ $0.947 \times 10^5$; $\epsilon_{532}$ $0.139 \times 10^5$.

EXAMPLE 4
ALKYLATION OF 3-AMINO-4-METHYLPHENOL WITH 3-CHLOROTRIFLUOROPROPANE

3-Amino-4-methylphenol, (61.5 g; 0.5 mole) (mp 149–50° C.), sodium acetate (41 g; 0.5 mole), 3-chlorotrifluoropropane (66.25 g; 0.5 mole) and 375 ml of deionized water were charged into a 1000 ml Parr Hastelloy C reactor, the reactor closed and purged with $N_2$ and heated to 150° C. with good stirring. A temperature in the range of 100–180° C. is acceptable. Pressure rose to 330 psi, then slowly fell during 20 hours at 150° C. to 160 psi. A pressure in the range of 100–500 psi is acceptable. The reactor was cooled in an ice bath and opened at 25° C. A pale yellow oily layer had formed. The aqueous layer had pH 4.2.

Pseudocumene (300 g) was added and the mixture stirred to dissolve the oil in it. Upon stirring for 1 hour, crystalline precipitate of unreacted 3-amino-4-methylphenol formed which was filtered off (15.5 g dry). The organic and aqueous layers were separated and the pseudocumene layer washed with 300 ml water giving 336 g of organic solution containing mostly monoalkylated 3-amino-4-methylphenol as shown by TLC on Silica Gel RPS-F using methanol/water, 1/9, as elutant. ($R_f$ 0.1).

NMR on an isolated sample of the product (oil) was consistent with the desired monoalkyl product. HPLC (reversed phase column with methanol/water elutant) indicated that this sample was about 94% monoalkyl containing about 3% dialkyl.

EXAMPLE 5

PREPARATION OF 9-(2-CARBOXYPHENYL)-3,6-BIS(3′,3′,3′TRIFLUOROPROPYLAMINO)-2,7-DIMETHYL XANTHYLIUM HYDROXIDE, INNER SALT

The pseudocumene layer from alkylation, containing 0.35–0.38 mole of 3-trifluoropropylamino-4-methylphenol was refluxed in a 1 L 3-necked flask fitted with thermometer, stirrer and Dean-Stark trap in order to remove water as the azeotrope. To the dry solution was added 30 g of phthalic anhydride. Condensation was effected by heating at reflux for 20 hours while removing water generated by reaction as the pseudocumene-water azeotrope. The solution turned red. When condensation was complete the solution was cooled to 100° C., 300 ml water and 25 g 50% sodium hydroxide added, and the pseudocumene removed by azeotropic distillation. The red dye which had crystallized out was separated by filtration and washed with 400 ml water (142 g wet paste). This filtercake was reslurried in 400 ml water and 10 g 50% sodium hydroxide, heated 30 minutes at 100.C, filtered again and washed with 400 ml water. Upon drying at 100° C, 40 g of dye zwitterion was obtained which melted at 258°–260° C.

EXAMPLE 6

PREPARATION OF 9-(2-METHOXYCARBONYLPHENYL)-3,6-BIS (3′, 3′, 3′-TRIFLUOROPROPYLAMIN)2,7-DIMETHYL-XANTHYLIUM FLUOROBORATE

To a 1000 ml flask was charged the 40 g crude zwitterion (from Example 5) and 500 g anhydrous methanol, and 50 g 100% sulfuric acid was dropped into the solution during 15 minutes with stirring. This solution was refluxed for 20 hours. Crystalline dye methyl ester methosulfate formed. On cooling in an ice bath more crystals formed. Filtration and washing with methanol, then water, gave, on drying at 100° C., 36.5 g, m.p. 307°–309° C. TLC vs. standard showed this product to contain 1–2% unesterified dye. Elemental analysis of the product by Schwarzkopf Microanalytical Laboratory gave the following results:

| For $C_{30}H_{30}F_6N_2O_7S$ | Theory | Found |
|---|---|---|
| (m.w. 676.64) | C 53.25 | 52.56 |
| | H 4.47 | 4.355 |
| | F 16.85 | 16.83 |
| | N 4.14 | 4.05 |
| | S 4.74 | 4.78 |

Recrystallization of a portion of this product, with clarification, from methanol gave red crystals which m. 312°–314° C. and contained less than 1% unesterified material according to TLC on Silica Gel plates (Analtech) using as elutant water:pyridine, 2:1. The product has $R_f$ 0.17 and unesterified R–10 has $R_f$ 0.75.

Dye methosulfate salt, mp 313°–314° C., (15 g) Was dissolved in 300 g methanol at the boiling point (62° C.) and clarified through Whatman No. 54 filter paper. A clarified solution of 2.84 g $NaBF_4$ in 25 ml water was prepared and added dropwise in about 10 minutes to the dye solution. Some red crystals formed. After stirring for 30 minutes with cooling to 40° C., the solution was still dark red. Additional water (75 g) was added dropwise in 15 minutes causing precipitation of most of the color. The mixture was stirred for 1 hour while cooling to 20° C. Filtration, washing the cake successively with 100 ml 50% methanol/water and 100 ml deionized water and drying in the oven at 120° C. for 16 hours gave red crystalline dye salt (12.5 g) which softened at 310° C. and melted at 312°–314° C.

The dye was recrystallized from methanol/water (1:1, v:v, 200 ml/g) and gave small red-brown crystals, mp 312°–314° with previous softening at 310° NMR (deuterodimethylsulfoxide): δ8.4–7.4 (m, 6H) resolved as 7.76 (broad t, 2H, J=5.9 Hz, N-H) and the rest as ring protons of the pendant aromatic group; 7.05 and 6.86 (d, 4H, xanthylium ring protons 1, 4, 5, 8); 3.75 (broad q, 4H, J=6.5 Hz, $CH_2$—N); 3.57 (s, 3H, O—$CH_3$); 2.74 (m, 4H, $CF_3$—$CH_2$); 2.11 (s, 6H, $CH_3$). Anal. calc. for $C_{29}H_{27}N_2O_3BF_{10}$: C, 53.39; H, 4.17; N, 4.30. Found: C, 53.56; H, 4.14; N, 4.29. Absorption in 190 proof alcohol: $\epsilon_{max}$ at 522 nm $1.128 \times 10^5$; $\epsilon_{488}$ $0.325 \times 10^5$; $\epsilon_{510.6}$ $0.778 \times 10^5$; $\epsilon_{514}$ $0.926 \times 10^5$; $\epsilon_{532}$ $0.769 \times 10^5$.

The foregoing description of the preferred embodiments of the subject invention have been presented for purposes of illustration and description and for a better understanding of the invention. It is not intended to be exhaustive or to limit the invention to the precise form disclosed; and obviously, many modifications and variations are possible in light of the above teaching. The particular embodiments were chosen and described in detail to best explain the principles of the invention and its practical application to thereby enable others skilled in the relevant art to best utilize the invention in various embodiments and with various modifications as are suited to the particular use contemplated. It is intended that the invention be defined by the claims appended hereto.

What is claimed is:

1. A compound of the formula

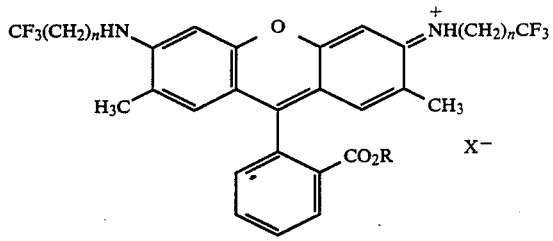

wherein R is hydrogen or linear or branched alkyl of 1 to 10 carbon atoms, n is an integer from 1 to 4, and X is an anion.

2. A compound according to claim 1 wherein n is 1 or 2.

3. A compound according to claim 2 wherein R is alkyl of 1 to 4 carbon atoms.

4. A compound according to claim 3 wherein R is methyl.

5. A compound according to claim 4 wherein n is 1.

6. A compound according to claim 4 wherein n is 2.

7. A compound according to claim 5 wherein X is fluoroborate.

8. A compound according to claim 6 wherein X is fluoroborate.

* * * * *